US005547458A

United States Patent [19]
Ortiz et al.

[11] Patent Number: 5,547,458
[45] Date of Patent: Aug. 20, 1996

[54] T-SHAPED ABDOMINAL WALL LIFT WITH TELESCOPING MEMBER

[75] Inventors: Mark S. Ortiz, Milford; Stephen J. Failla, Cincinnati, both of Ohio

[73] Assignee: Ethicon, Inc., Cincinnatti, Ohio

[21] Appl. No.: 273,452

[22] Filed: Jul. 11, 1994

[51] Int. Cl.⁶ .................................................. A61B 17/02
[52] U.S. Cl. ...................... 600/204; 600/215; 600/219; 604/107; 606/191; 606/198
[58] Field of Search ............................ 128/3, 17, 20; 606/191, 198; 604/104–109

[56] References Cited

U.S. PATENT DOCUMENTS

| | | |
|---|---|---|
| 1,798,124 | 3/1931 | Hunn . |
| 2,841,148 | 7/1958 | Kadavy . |
| 3,099,544 | 7/1963 | Sheesley . |
| 3,831,587 | 8/1974 | Boyd . |
| 3,863,639 | 2/1975 | Kleaveland . |
| 3,888,117 | 6/1975 | Lewis . |
| 4,052,980 | 11/1977 | Grams et al. . |
| 4,151,838 | 5/1979 | Crew . |
| 4,232,660 | 11/1980 | Coles . |
| 4,291,687 | 9/1981 | Sinnreich . |
| 4,610,243 | 9/1986 | Ray . |
| 4,616,633 | 10/1986 | Vargas Garcia . |
| 4,616,634 | 10/1986 | Vargas Garcia . |
| 4,705,040 | 11/1987 | Mueller et al. . |
| 4,889,107 | 12/1989 | Kaufman . |
| 4,945,897 | 8/1990 | Greenstein et al. . |
| 5,026,389 | 6/1991 | Thieler . |
| 5,080,893 | 1/1992 | Goldberg et al. . |
| 5,151,086 | 2/1992 | Duh et al. . |
| 5,152,279 | 10/1992 | Wilk ..................................... 128/17 |
| 5,183,033 | 2/1993 | Wilk . |
| 5,183,465 | 2/1993 | Xanthakos et al. . |
| 5,195,505 | 3/1993 | Josefson ............................... 128/20 |
| 5,275,610 | 1/1994 | Eberbach . |
| 5,280,782 | 1/1994 | Wilk ..................................... 600/214 |
| 5,353,785 | 11/1994 | Wilk . |
| 5,361,752 | 11/1994 | Moll et al. ............................. 128/20 |

FOREIGN PATENT DOCUMENTS

| | | |
|---|---|---|
| 0246086 | 5/1987 | European Pat. Off. . |
| 661403 | 6/1938 | Germany . |
| WO91/14392 | 10/1991 | WIPO . |
| WO92/21291 | 12/1992 | WIPO . |
| WO92/21292 | 12/1992 | WIPO . |
| WO92/21293 | 12/1992 | WIPO . |
| WO92/21294 | 12/1992 | WIPO . |
| WO92/21295 | 12/1992 | WIPO . |
| WO92/21298 | 12/1992 | WIPO . |
| WO93/25148 | 12/1993 | WIPO . |

OTHER PUBLICATIONS

Kitano et al., "A Safe And Simple Method To Maintain A Clear Field Of Vision During Laparoscopic Cholecystectomy" from *Surgical Endoscopy* (1992) 6: 197–198.

Hashimoto et al., "Laparoscopic Cholecystectomy: An Approach Without Pneumoperitoneum" from *Surgical Endoscopy*(1993) 7: 54–56.

(List continued on next page.)

*Primary Examiner*—Richard J. Apley
*Assistant Examiner*—Kelly McGlashen
*Attorney, Agent, or Firm*—Dressler, Goldsmith, Shore & Milnamow, Ltd.

[57] ABSTRACT

Abdominal wall lift devices and methods are disclosed that extend a lift device through an opening in the abdominal wall in an entry configuration and subsequently transform the device to a deployed configuration within the abdominal cavity. One embodiment includes a plurality of elongated bar members that may be introduced into an abdominal cavity in a separated end-to-end orientation. The bar members are subsequently interconnected into a deployed configuration within the abdominal cavity. Another embodiment includes a device that may be introduced through a small opening in an abdominal wall in a generally L-shaped configuration and subsequently deployed into a generally T-shaped configuration within the abdominal cavity. A further embodiment includes an umbrella-like device that may be introduced in a slender generally cylindrical configuration and subsequently deployed into an open umbrella-type configuration.

2 Claims, 4 Drawing Sheets

OTHER PUBLICATIONS

Akimaru et al., "Subcutaneous Wire Traction Technique With $CO_2$ Insufflation For Laparoscopic Cholecystectomy" from *Journal of Laparoendoscopic Surgery* (1993) 3: 59–62.

Banting et al., "Abdominal Wall Lift" from *Surgical Endoscopy* (1993) 7: 57–59.

Automated Medical Products Corp. brochure entitled "Iron Intern".

Automated Medical Products Corp. brochure entitled "Colon Resection".

Automated Medical Products Corp. brochure entitled "Abdominal Aortic Aneurysm".

Automated Medical Products Corp. brochure entitled "Anterior Colon Resection".

Automated Medical Products Corp. brochure entitled "Electrocoagulation of Rectal Tumors".

Automated Medical Products Corp. brochure entitled "Kidney Transplants".

Automated Medical Products Corp. brochure entitled "Laparoscopic Surgery".

Automated Medical Products Corp. brochure entitled "Vaginal Hysterectomy".

Davis & Geck Endosurgery brochure entitled "Count on US".

Origin Medsystems, Inc. brochure entitled "Gasless Laparoscopy".

Societe 3X brochure entitled "Le Pneumoperitoine En Suspension".

Societe 3X brochure entitled "Technical Notes Concerning The Suspender of the Abdominal Wall".

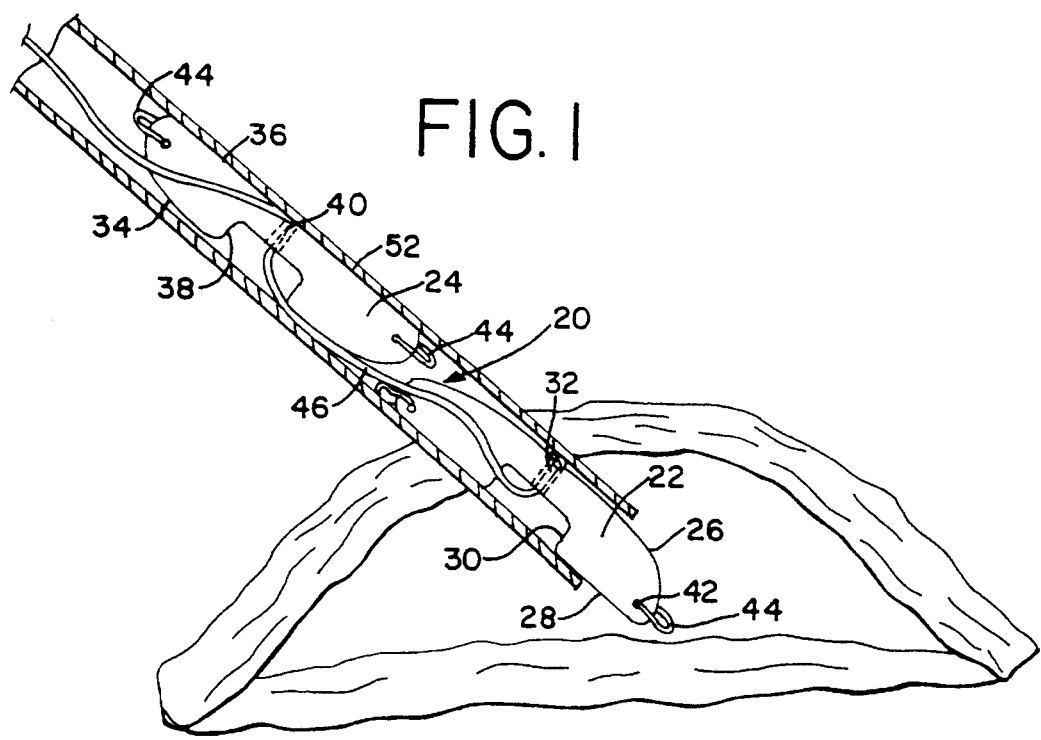
FIG. 1
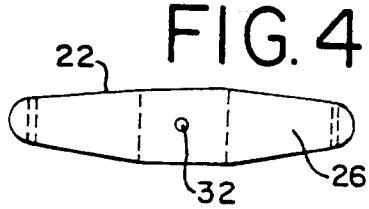
FIG. 4
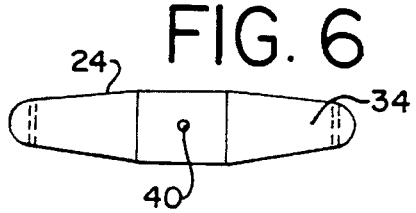
FIG. 6
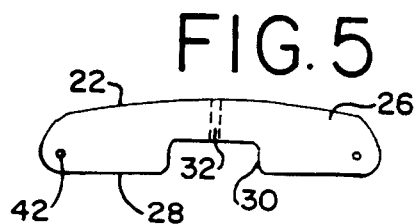
FIG. 5
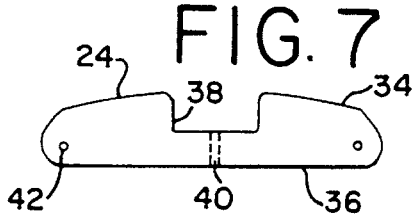
FIG. 7
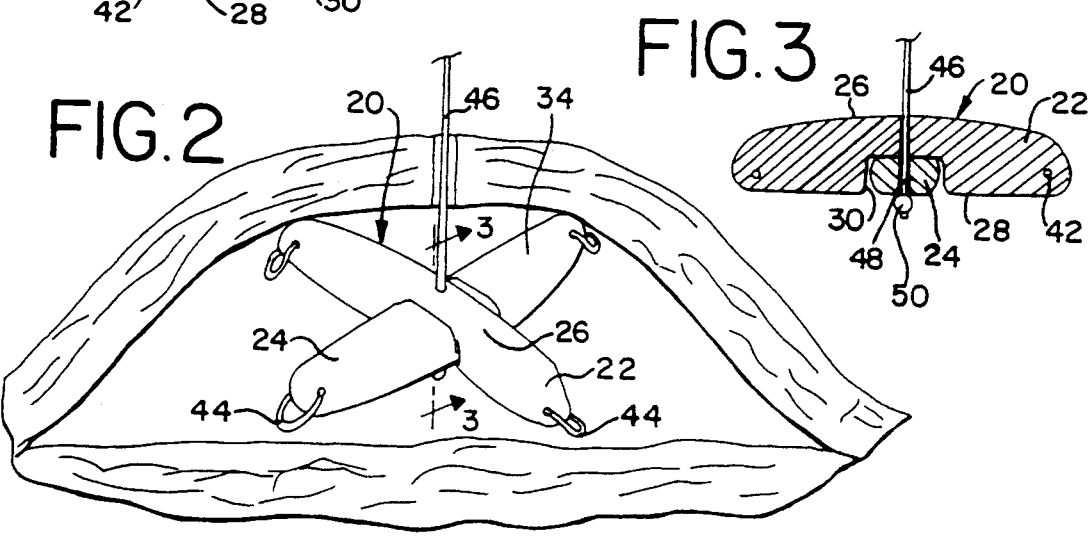
FIG. 2
FIG. 3

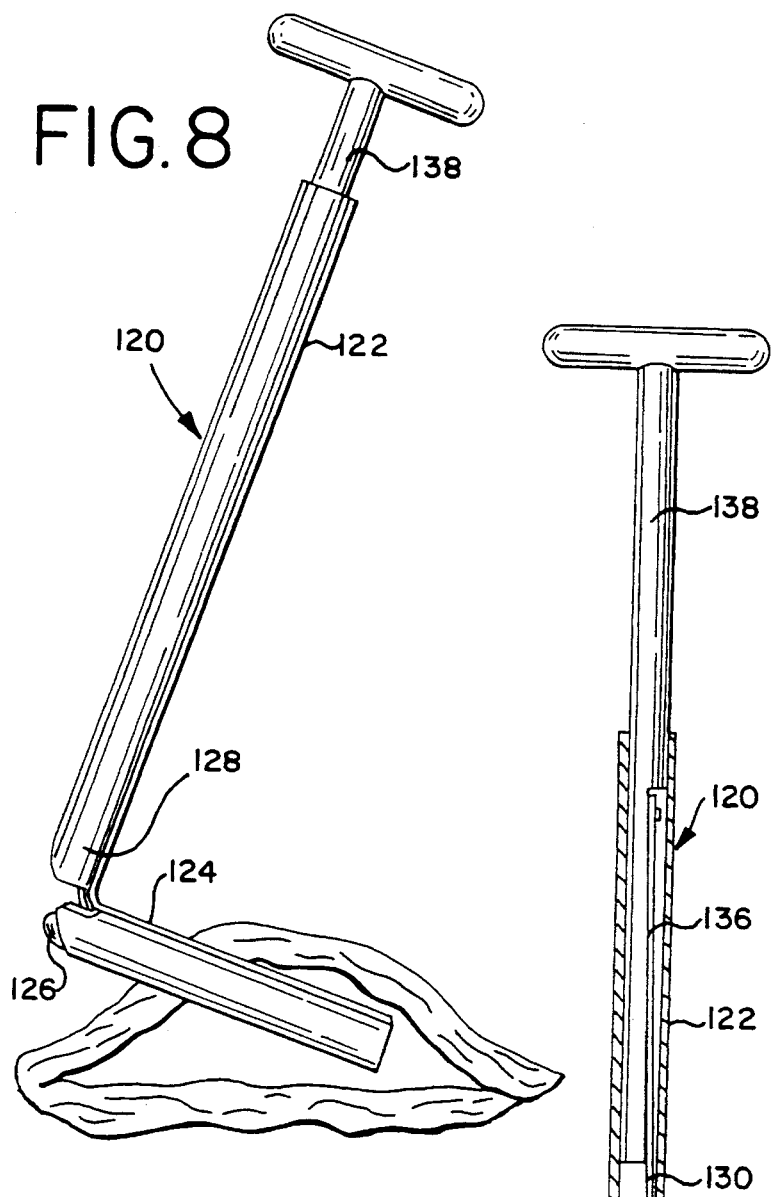

T-SHAPED ABDOMINAL WALL LIFT WITH TELESCOPING MEMBER

FIELD OF THE INVENTION

This invention relates generally to surgical methods and devices and, more particularly, to methods and devices for lifting an abdominal wall during laparoscopic surgical and diagnostic procedures.

BACKGROUND OF THE INVENTION

Laparoscopic surgical procedures have been around for many years and have become more available due to advances in technology relating to the laparoscope or video imaging system. They are much less intrusive to the patient than typical open surgical procedures. While an open surgical procedure may involve one primary incision that is at least 6–20 centimeters long, a laparoscopic procedure typically uses smaller incisions, each only around 5–11 millimeters long. In open surgery, the surgeon cuts muscle. In laparoscopic surgery, the surgeon generally does not cut muscle. Because they are less intrusive than open surgical procedures, laparoscopic procedures have resulted in much shorter surgical procedures and recovery times.

Laparoscopic procedures have typically involved insufflation of the abdominal or peritoneal cavity with carbon dioxide and/or other gases in order to create a pneumoperitoneum. The pneumoperitoneum establishes an open space inside the peritoneal cavity to enable the surgeon to move the laparoscope and laparoscopic instruments around the inside and perform surgical and diagnostic procedures.

Typically, the pneumoperitoneum is established by puncturing the abdominal wall with a Veress needle and injecting gas from an insufflator through the Veress needle into the peritoneal cavity to a pressure of around 12 mm Hg.

After insufflation, a trocar is advanced through the opening in the abdominal wall and into the peritoneal cavity. The trocar includes a tube or cannula that usually has a gaseous seal to contain the carbon dioxide within the peritoneal cavity and maintain insufflation. The cannula is used for insertion of other medical instruments such as a laparoscope therethrough and into the peritoneal cavity.

There may be certain difficulties associated with insufflation of the peritoneal cavity. A major consideration is operative and postoperative pain which patients may experience in the abdomen or shoulder area due to migrating gas. This occurs when insufflation causes excess gas pressure in the peritoneal cavity. Excess gas pressure may also compress the pleural cavities thus making respiration difficult. Other possible difficulties associated with insufflation in laparoscopic surgery include subcutaneous emphysema, blood vessel penetration, etc.

The attendant difficulties of insufflation have led to alternatives to insufflation wherein an open space is established by elevating the abdominal wall with a mechanical lift. The lift is introduced through an opening in the abdominal wall into the peritoneal cavity before establishing an open space. The lift is elevated mechanically in order to distend the abdominal wall. When the abdominal wall is distended, ambient air enters the abdomen through the puncture opening in the abdominal wall and an open space at or near ambient air pressure is established.

By establishing an open space at ambient air pressure, insufflation and the concomitant need for gaseous seals in endoscopic instruments and trocars for maintaining a relatively high gas pressure in the peritoneal cavity is eliminated. Thus the attendant difficulties of insufflation, as well as the need for costly equipment, is eliminated.

The prior art includes several abdominal lift structures. Origin Medsystems, Inc. of Menlo Park, Calif. markets a lift under the trademark Laparofan™. It has two radially extending blades that are rotatable. The blades are closed together for initial insertion into the abdominal cavity. After insertion, the blades are spread or fanned. When the lift is elevated, the blades contact and elevate the inner surface of the abdominal wall. Origin's device is described in International Patent Application PCT/FR91/4456.

Societe 3X, a French company, markets an abdominal lift and support structure. This lift is shown and described in International Patent Application PCT/FR91/227. It contains a series of curves forming a generally triangular shape. The tip of the lift is turned downwardly slightly. The support structure has a crane and boom design. Gross adjustments are made by sliding the supporting leg and the boom within their respective holders. A mechanical screw-jack is used for fine adjustment.

International Patent Application PCT/FR91/227 describes an abdominal lift having various curves in different directions. U.S. Pat. No. 5,183,033 describes a method for lifting an abdominal wall with a set of linear and non-linear abdominal lifts. International Patent Application PCT/US/4392 describes a variety of mechanical rods, arms and/or balloons for mechanically lifting an abdominal wall during laparoscopic surgery.

There are some other prior art structures for elevating and/or supporting abdominal lifts in laparoscopic surgery. U.S. Pat. No. 5,183,033 illustrates support structures using winches or U-shaped bars for use in laparoscopic surgery.

Further, there are a number of prior art support structures for supporting mechanical lifts used in open surgery. For example, see U.S. Pat. Nos. 5,109,831 and 4,143,652.

An improved abdominal lift device is disclosed in U.S. patent application Ser. No. 08/108,895, filed on Aug. 18, 1993, and assigned to the same assignee as the present invention. The device includes a curved portion that defines a substantial portion of a circle. A spoke portion extends radially inwardly from the curved portion and an upstanding member extends upwardly from the spoke portion. The upstanding member is connectable to a support structure which elevates and supports the abdominal lift device.

The ease of operation of most of these prior art lift devices without any damage to internal viscera is limited. There is a need for lift devices that may be directed through a small opening in an abdominal wall and subsequently deployed within the abdominal cavity. There is also a need for an alternative surgical lift method and device that may be used by doctors in a hospital operating room and in their offices for diagnostic purposes. It is anticipated that such diagnostic procedures may include the use of a Veress needle-type device having optical capabilities without the use of a general anesthesia.

SUMMARY OF THE INVENTION

In accordance with a first preferred embodiment of the invention, an abdominal wall lift device is provided that includes a plurality of elongated bar members that may be introduced into an abdominal cavity through a trocar or small opening in a separated end-to-end orientation. Once within the abdominal cavity, the bar members are interconnected to form a lift device.

The lift device includes a first elongated bar member and a second elongated bar member. The first bar member has a generally transverse recess portion formed into a lower surface thereof and the second bar member has a generally transverse recess portion formed into an upper surface thereof. A flexible suture is connected at one end thereof to the second bar member and extends through an opening formed through the recess portion in the first bar member so as to permit the bar members to move between first and second positions. In their first positions, the bar members are generally in an end-to-end relationship to facilitate their passage into and out of an abdominal cavity. In their second positions, the bar members are within the abdominal cavity and the recess portion of the first bar member is received within the recess portion of the second bar member so as to position them perpendicular to one another in substantially the same horizontal plane. The bar members may be provided with means to facilitate the grasping and removal thereof by a grasping instrument.

In accordance with a second preferred embodiment of the invention, an abdominal wall lift device is provided that may be introduced into the abdominal cavity through a small opening in the abdominal wall in a generally L-shaped configuration. Once within the abdominal cavity, the lift device may be deployed into a generally T-shaped configuration.

The lift device includes a first elongated tubular member and a second elongated tubular member connected together to form a generally L-shaped configuration. An extension rod is slidably received within the second tubular member and is selectively movable between first and second positions. In its first position, the rod member is substantially received within the second tubular member to facilitate insertion of the device into an abdominal cavity. In its second position, the rod member extends outwardly from the second tubular member such that the second tubular member and the rod member form a generally T-shaped configuration with the first tubular member for deployment of the device within an abdominal cavity. A flexible control link member is connected to the rod member for selectively moving the rod member between its first and second positions.

In accordance with a third preferred embodiment of the invention, an umbrella-like abdominal wall lift device is provided that may be introduced into the abdominal cavity through a small opening in the abdominal wall in a slender generally cylindrical configuration. Once within the abdominal cavity, the lift device may be deployed into an open umbrella-type configuration.

The lift device inches an upper hub member and a lower hub member. A plurality of radially spaced apart links extend between the upper and lower hub members. The links have first end portions connected to the upper hub member and second end portions connected to the lower hub member. The links are movable between a first entry configuration and a second deployment configuration. The links in their first entry configuration have intermediate portions thereof that are substantially in lineal alignment with the end portions thereof as the upper and lower hub members move away from one another. The links in their second deployment configuration have intermediate portions that extend radially outwardly from the end portions thereof as the upper and lower hub members move toward one another. The links may comprise first and second link members which are pivotally connected to one another at the intermediate portions of the links. Alternatively, the links may comprise either a flexible member or a member having a living hinge formed at an intermediate portion thereof. A flexible suture is connected at one end thereof to the lower hub member and extends through an opening formed in the upper hub member to control movement of the links between their first and second configurations.

The present invention also provides unique methods for lifting and holding an abdominal wall portion in an elevated position to perform a diagnostic or surgical procedure in an abdominal cavity. In accordance with one method, at least two elongated bar members, oriented in an end-to-end separated relationship, are directed through a small opening in the abdominal wall into the abdominal cavity. The bar members are oriented relative to one another within the abdominal cavity to form an interconnected deployed lift assembly wherein the bar members are substantially in the same horizontal plane. The deployed lift assembly is lifted and held in an elevated position to hold the abdominal wall in an elevated position. After the diagnostic or surgical procedure is performed, the bar members are disconnected from one another and separately removed from the abdominal cavity through a small opening in the abdominal wall. The bar members may be interconnected by a flexible suture such that an initial application of an upward force to the suture moves the bar members into their deployed configuration and a continued application of an upward force lifts the deployed lift assembly into its elevated position.

In accordance with an alternative method, an elongated needle is attached to an abdominal lift device that has an entry configuration and a deployed configuration. The needle and the lift device are directed through a small opening or cannula in an abdominal wall to position the lift device within the abdominal cavity in its entry configuration. The lift is transformed from its entry configuration to its deployed configuration within the abdominal cavity. The needle is directed from the abdominal cavity so as to create a small opening in the abdominal wall and pass therethrough while the deployed lift device is maintained positioned in the abdominal cavity. The lift device is lifted and held in an elevated position so as to hold the abdominal wall in an elevated position. After performing a diagnostic or surgical procedure, the lift device is transformed from its deployed configuration to its entry configuration and removed from the abdominal cavity through a small opening in the abdominal wall. The lift device is preferably transformed from its entry configuration to its deployed configuration upon contacting an inner surface of the abdominal wall after the needle is withdrawn from the abdominal cavity. The lift device is preferably transformed from its deployed configuration into its entry configuration upon contacting an inner surface of the abdominal wall adjacent the small opening or cannula through which the lift device is removed from the abdominal cavity.

These and other aspects and attributes of the present invention will be discussed with reference to the following drawings and accompanying specification.

BRIEF DESCRIPTION OF THE DRAWINGS

FIG. 1 is an elevational view, partially in section, of an abdominal wall lift device constructed in accordance with a first preferred embodiment of the invention, that is shown in its entry configuration being inserted through an introducing cannula into an abdominal cavity;

FIG. 2 is a perspective view of the lift device of FIG. 1 shown in a deployed configuration extending into an abdominal cavity;

FIG. 3 is a cross-sectional view taken along line 3—3 in FIG. 2;

FIG. 4 is a top plan view of the top cross bar member of the lift device of FIG. 2;

FIG. 5 is an elevational view of the top cross bar member as shown in FIG. 4;

FIG. 6 is a top plan view of the bottom cross bar member of the lift device of FIG. 2;

FIG. 7 is an elevational view of the bottom cross bar member as shown in FIG. 6;

FIG. 8 is an elevational view of an abdominal wall lift device constructed in accordance with a second preferred embodiment of the invention, that is shown in its entry configuration being directed into an abdominal cavity;

FIG. 9 is an elevational view, partially in section, of the lift device of FIG. 8 in its deployed configuration extending into an abdominal cavity;

DETAILED DESCRIPTION OF THE PREFERRED EMBODIMENTS

Figure 10:
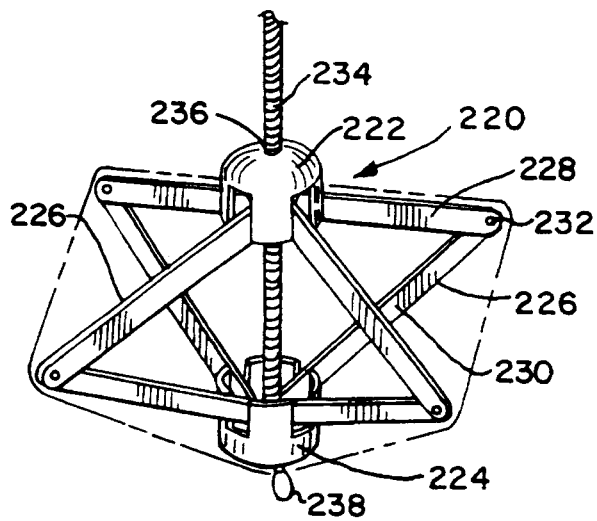
FIG. 10 is a perspective view of an abdominal wall lift device constructed in accordance with a third preferred embodiment of the invention shown in its deployed configuration.

While this invention is susceptible of embodiment in many forms, there is shown in the drawings, and will be described herein in detail, specific embodiments thereof with the understanding that the present disclosure is to be considered as an exemplification of the principles of the invention and is not intended to limit the invention to the specific embodiments illustrated.

Referring to FIGS. 1–7, an abdominal wall lift device 20, constructed in accordance with a first preferred embodiment of the invention, includes a first elongated bar member 22 and a second elongated bar member 24.

Bar member 22 has a contoured generally concave shaped upper surface 26 and a generally flat lower surface 28. A transverse recess portion 30 is formed into the lower surface 28. A vertical opening 32 extends through bar member 22 at recess portion 30. Bar member 24 has a contoured generally concave shaped upper surface 34 and a generally flat lower surface 36. A transverse recess portion 38 is formed into the upper surface 34. A vertical opening 40 extends through bar member 24 at recess portion 38. The end portions of the bar members 22 and 24 have substantially horizontal openings 42 formed therein through which grasping loops 44 are received.

The bar members 22 and 24 are connected together by a flexible suture member 46 that extends through the openings 32 and 40. A distal end portion 48 of suture member 46 extends through opening 40 and is prevented from passing therethrough by a suitable means such as a knot or a retent ball 50. Opening 32 is dimensioned so as to permit suture member 46 to freely slide therethrough along a portion of its length.

Referring to FIGS. 1 and 2, the bar members 22 and 24 are respectively shown in their first entry positions and their second deployment positions. In their entry positions, the bar members 22 and 24 are generally in an end-to-end orientation to facilitate entry into an abdominal cavity through a small opening in the abdominal wall. In their deployment positions, the recess portion 30 of the bar member 22 is received within the recess portion 38 of the bar member 24 so as to position the bar members perpendicular to one another in substantially the same horizontal plane. The lower surfaces 28 and 36 are in substantially the same plane and the upper surfaces 26 and 34 form a generally concave contour.

The unique features of the lift device 20 will become more apparent from the following brief discussion of a method of deployment of the device within an abdominal cavity. The bar members 22 and 24, oriented in their first position end-to-end orientation, are directed through a small opening in an abdominal wall into an abdominal cavity. As shown in FIG. 1, one way of inserting the bar members is through a suitable trocar or cannula 52. Once the bar members are within the abdominal cavity, the suture 46 is slowly lifted so as to cause the bar members to assume their second deployment configuration, as shown in FIG. 2. The bar members are configured and weighted so as to cause them to automatically slide into their deployment configuration without the need to individually position one with respect to the other. The abdominal wall may then be lifted and held in an elevated position by lifting the suture member 46 and the bar members 22 and 24 attached thereto. Depending on the procedure to be performed, it is anticipated that a plurality of the lift devices 20 may be deployed to create the necessary pneumoperitoneum. Upon completion of the diagnostic or surgical procedure, the suture member 46 and the bar members 22 and 24 are lowered causing the abdominal wall to return to its normal position. The bar members 22 and 24 may then be removed from the abdominal cavity in a suitable manner, such as by directing a grasper device into the abdominal cavity to grasp the loops 44 and pull the bar members out through a small opening in the abdominal wall. It is anticipated that the small openings in the abdominal wall through which the bar members are inserted and removed may also be used to direct surgical and diagnostic instruments into the abdominal cavity during the procedure to be performed. In so doing, the number of openings is kept to a minimum.

Referring to FIGS. 8 and 9, an abdominal wall lift device 120 constructed in accordance with a second preferred embodiment of the invention, includes a first elongated tubular member 122, a second elongated tubular member 124, and an extension rod member 126. Tubular member 124 is oriented substantially perpendicular to the distal end portion 128 of tubular member 122 so as to define a generally L-shaped configuration.

Extension rod member 126 is slidably received within tubular member 124. Rod member 126 is movable between a first position and a second position. When in its first position, rod member 126 is substantially received within tubular member 124 to facilitate insertion of the device into an abdominal cavity, as shown in FIG. 8. When in its second position, rod member 126 extends substantially outwardly from the tubular member 124, such that tubular member 124 and rod member 126 form a generally T-shaped configuration with tubular member 122 for deployment of the device within an abdominal cavity, as shown in FIG. 9.

A flexible spring steel control link member 130 is operatively connected to rod member 126 for selectively moving the rod member between its first and second positions. Link member 130 has a first or distal portion 132 that is suitably connected to an inner portion 134 of rod member 126 and a second or proximal portion 136 that extends into and is longitudinally movable within tubular member 122. A handle member 138 is operatively connected to the proximal portion 136 of link member 130. As handle member 138 moves the end portion 136 of link member 130 toward the distal end portion 128 of tubular member 122 the rod member 126 moves toward its first position, as shown in FIG. 8. As handle member 138 moves the end portion 136 of link member 130 toward the proximal end portion 129 of tubular member 122 the rod member 126 moves toward its second position, as shown in FIG. 9.

The unique features of the lift device 120 will become more apparent from the following brief discussion of a method of deployment of the device within an abdominal cavity. With the device oriented with the rod member 122 in its first position substantially within tubular member 124, the tubular member 124 is directed through a small opening in the abdominal wall into the abdominal cavity, as shown in FIG. 8. The device 120 is then deployed by operating the handle member 138 so as to move the end portion 136 of link 130 toward the proximal end portion 129 of tubular member 122 and thereby move the rod member 126 toward its second position, as shown in FIG. 9. The abdominal wall may then be lifted and held in an elevated position by lifting and supporting the device 120. It is anticipated that a plurality of devices 120 may be deployed to create the necessary open space. Upon completion of the procedure, the handle member 138 is operated to move the end portion 136 of link member 130 toward the distal end portion 128 of tubular member 122 so as to move rod member 126 back into its first position, as shown in FIG. 8. The device may then be removed through the small opening in the abdominal wall.

Figure 14:
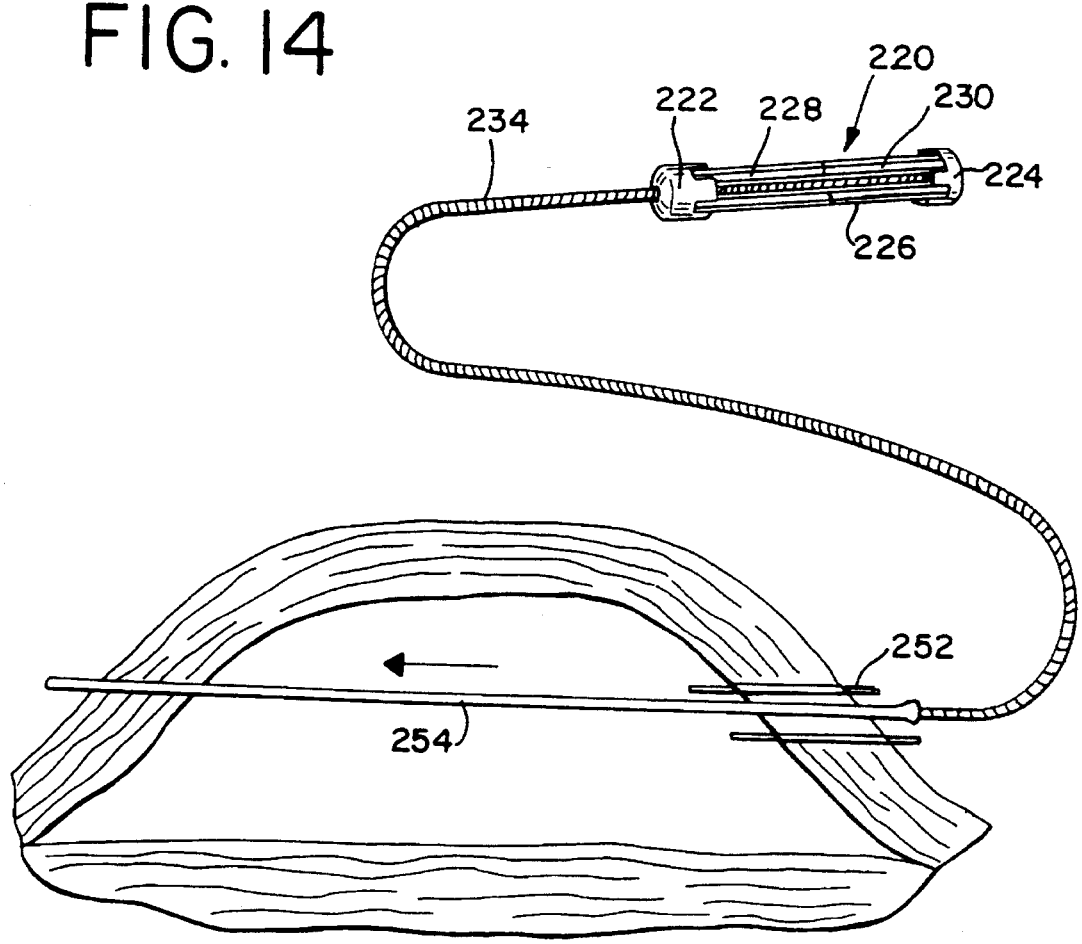
FIG. 14 is a perspective view showing the introduction of an abdominal wall lift device of the type shown in FIG. 10 in accordance with a method of the present invention.
Figure 15:
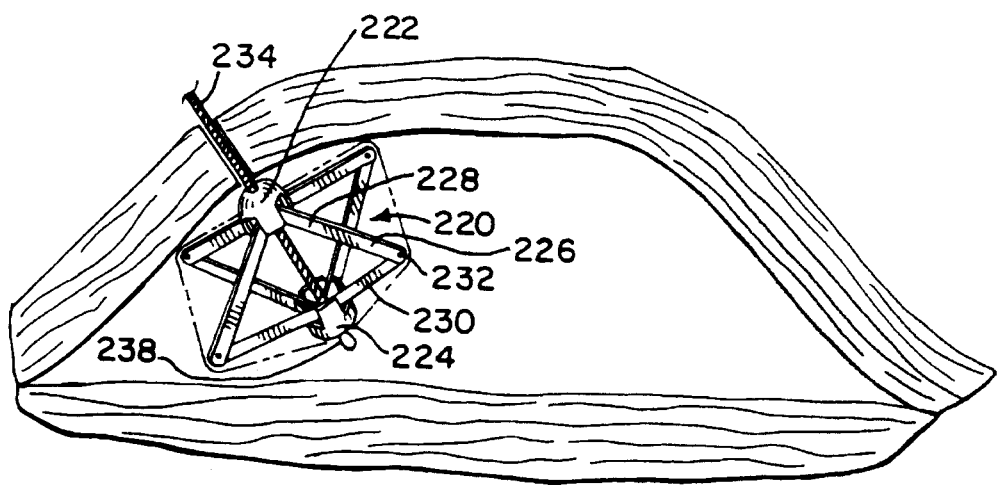
FIG. 15 is a perspective view similar to FIG. 14 showing the abdominal wall lift device in its deployed configuration.

Referring to FIGS. 10, 14 and 15, an abdominal wall lift device 220, constructed in accordance with a third preferred embodiment of the invention, includes an upper hub member 222, a lower hub member 224 and a plurality of radially spaced links 226 that extend between the upper and lower hub members.

Each of the links 226 comprise a first link member 228 and a second link member 230. Link members 228 and 230 have first end portions that are respectively pivotally secured to the hub members 222 and 224 in a suitable manner (not shown) and second end portions that are pivotally secured to one another at intermediate portions 232 of the links 226. As will hereinbelow become more apparent, the links 226 are movable between a first entry configuration and a second deployment configuration. In the entry configuration the second end portions of the link members 228 and 230 are substantially in lineal alignment with the first end portions of the link members 228 and 230, as the upper and lower hub members 222 and 224 are moved away from one another, as shown in FIG. 14. In the deployment configuration, the second end portions of the link members 228 and 230 extend radially outwardly from the first end portions of the link members 228 and 230, as the upper and lower hub members 222 and 224 are moved away from one another, as shown in FIGS. 10 and 15.

A flexible suture member 234 is suitably connected at one end thereof to lower hub member 224 and extends through an opening 236 formed in upper hub member 222, to control the movement of the links 226 between their first and second configurations. A grasping loop 238 is suitably attached to a lower portion of lower hub member 224. As will hereinbelow become more apparent in a discussion of a unique method of the invention, when the links 226 are in their first configurations, and the upper hub member 222 is in a substantially fixed position, upward movement of the suture 234 pulls the lower hub member 224 toward the upper hub member 222 causing the links 226 to move into their second configurations. Pulling of the lower hub member 224 through a small opening or cannula in the abdominal wall causes portions of the link members 230 to contact the edges of the opening or cannula, causing the links 226 to move into their first positions as the device is removed from an abdominal cavity.

Figure 11:
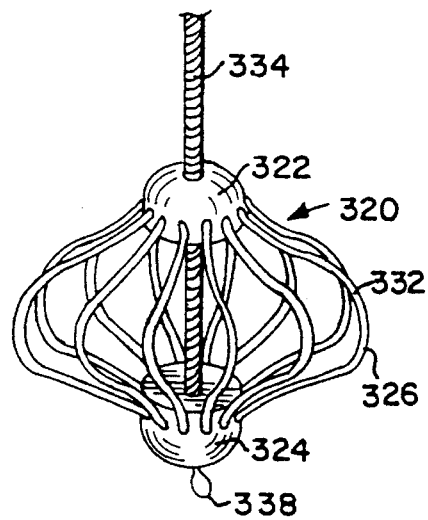
FIG. 11 is a perspective view of an abdominal wall lift device constructed in accordance with a fourth preferred embodiment of the invention shown in its deployed configuration.

Referring to FIG. 11, an abdominal wall lift device 320, constructed in accordance with a fourth preferred embodiment of the invention, is similar in construction and operation to lift device 220. Accordingly, in order to simplify the disclosure of the construction and operation thereof, the corresponding elements are identified with reference numerals having the same last two digits, and the above disclosure of such elements is incorporated herein by reference. Lift device 320 includes an upper hub member 322, a lower hub member 324, and a plurality of radially spaced links 326 that extend between the upper and lower hub members. The links 326 are flexible members that have respective end portions suitably secured to the upper and lower hub members. The links are movable between a first entry configuration, wherein the intermediate portions 332 thereof are substantially in lineal alignment with the end portions, and a second deployment configuration, wherein the intermediate portions 332 extend radially outwardly from the end portions, as shown in FIG. 11. A flexible suture 334 is connected at one end thereof to lower hub member 324 and extends through an opening 336 formed in upper hub member 322. A grasping loop 338 is suitably attached to a lower portion of lower hub member 334.

Figure 12:
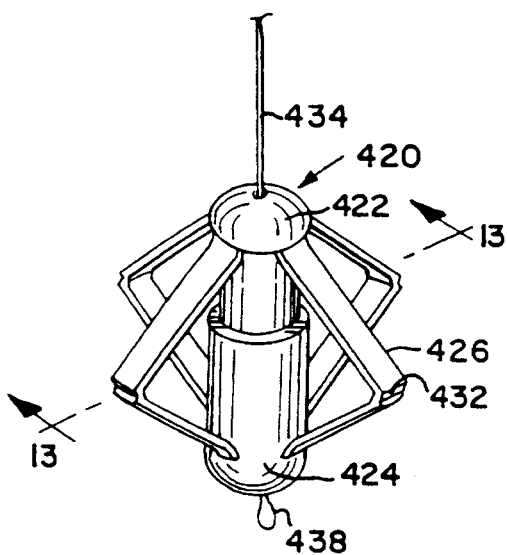
FIG. 12 is a perspective view of an abdominal wall lift device constructed in accordance with a fifth preferred embodiment of the invention shown in its deployed configuration.
Figure 13:
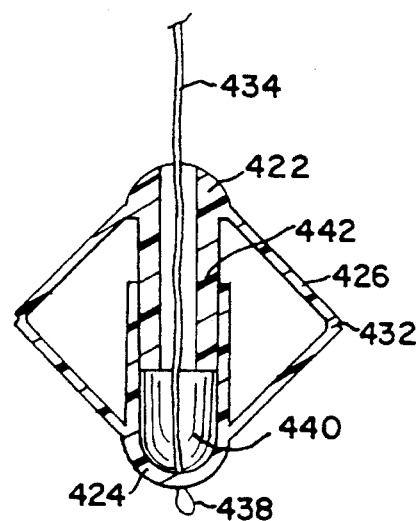
FIG. 13 is a cross-sectional view taken along line 13—13 in FIG. 12

Referring to FIGS. 12 and 13, an abdominal wall lift device 420, constructed in accordance with a fifth preferred embodiment of the invention, is also similar in construction and operation to lift device 320. Accordingly, the corresponding elements are identified with reference numerals having the same last two digits, and the above disclosure of such elements is incorporated herein by reference. Lift device 420 includes an upper hub member 422, a lower hub member 424, and a plurality of radially spaced links 426 that extend between the upper and lower hub members. The links 426 have end portions that are respectively secured to the upper and lower hub members and intermediate portions 432 that define living hinges. The links are movable between a first entry configuration, wherein the intermediate portions 432 thereof are substantially in lineal alignment with the end portions, and a second deployment configuration, wherein the intermediate portions extend radially outward from the end portions, as shown in FIGS. 12 and 13. A flexible suture 434 is connected at one end thereof to lower hub member 424 and extends through an opening 436 formed in upper hub member 422. A grasping loop 438 is suitably attached to a lower portion of lower hub member 434. In order to control and guide the relative movement of the upper and lower hub members towards and away from one another, the lower hub member 424 is formed so as to define a socket portion 440 into which is slidably received a stem portion 442 formed in the upper hub member 422.

The unique features of the lift devices 220, 320 and 420 will become more apparent from the following brief discussion of a method of deployment of such devices within an abdominal cavity. Although the method will be specifically disclosed with respect to lift device 220, it will be understood by one skilled in the art that such method is also applicable to the devices 320 and 420.

Referring to FIG. 14, there is shown an abdominal wall lift device 220 in its first entry configuration being inserted through a cannula 252 passing through an abdominal wall for entry into an abdominal cavity. A proximal portion of suture member 234 is attached to an elongated needle 254. The needle 254 and the lift device 220 are directed through the cannula 252 into the abdominal cavity. The distal end of needle 254 is directed through a portion of the abdominal wall opposed to the cannula 252 maintaining the lift device in the abdominal cavity. As the suture member 234 is directed through the abdominal wall, the leading surface of upper hub member 222 is moved into contact with the inner surface of the abdominal cavity. Continued externalization of suture member 234 causes lower hub member 224 to be urged toward upper hub member 222 so as to move the links 226 into their second deployment configuration, as shown in FIG. 15. The abdominal wall may then be lifted and held in an elevated position by lifting the suture member 234 and the lift device 220 attached thereto. Depending on the procedure to be performed, it is anticipated that a plurality of the lift devices 220 may be deployed to create the necessary pneumoperitoneum. Upon completion of the diagnostic or surgical procedure, the suture member 234 is lowered causing the abdominal wall to return to its normal position. The lift device 220 may then be removed from the abdominal cavity by directing a suitable instrument, such as a grasper, through the cannula 252 to grasp the loop 238. As the grasper is removed through the cannula, portions of the links 226, such as link members 230, contact the distal edges of the cannula so as to cause the link members to move into their first entry configuration and thereby permit the lift device to pass through the cannula.

From the foregoing, it will be observed that numerous modifications and variations can be effected without departing from the true spirit and scope of the novel concept of the present invention. It is to be understood that no limitation with respect to the specific embodiment is intended or should be inferred. The disclosure is intended to cover by the appended claims all such modifications as fall within the scope of the claims.

What is claimed is:

1. An abdominal wall lift device, comprising:

a first elongated tubular member having a distal end portion and a proximal end portion;

a second elongated tubular member having a first end portion and a second end portion, said first end portion of said second elongated tubular member being connected to said first elongated tubular member at said distal end portion of said first elongated tubular member such that said first and second elongated tubular members are in a generally L-shaped configuration;

an extension rod member telescopically received within said second elongated tubular member, said extension rod member being movable between a first position wherein said rod member is substantially received within said second elongated tubular member to facilitate insertion of the device into an abdominal cavity and a second position wherein said rod member extends substantially outwardly from said first end portion of said second elongated tubular member such that said second elongated tubular member and said rod member form a generally T-shaped configuration with said first elongated tubular member for deployment of said device within an abdominal cavity;

a control link member connected to said rod member to selectively move said rod member within said second elongated tubular member between its first and second positions; and said rod member includes an inner portion and an outer portion, said control link member being flexible and having a first end portion connected to said inner portion of said rod member and a second end portion that extends into and is longitudinally movable within said first elongated tubular member such that as said second end portion of said control link member moves toward said distal end portion of said first elongated tubular member said rod member moves toward its first position and as said second end portion of said control link member moves toward said proximal end portion of said first elongated tubular member said rod member moves toward its second position.

2. An abdominal wall lift device in accordance with claim 1 wherein a handle member extends into said first elongated tubular member, said handle member being operatively connected to said second end portion of said control link member for selectively moving said second end portion of said control link member toward said distal and proximal ends of said first elongated tubular member.

* * * * *